United States Patent
Wu et al.

(10) Patent No.: US 12,064,599 B2
(45) Date of Patent: Aug. 20, 2024

(54) MANAGEMENT OF INSUFFICIENT HYPOGLYCEMIA RESPONSE

(71) Applicant: Medtronic MiniMed, Inc., Northridge, CA (US)

(72) Inventors: Di Wu, Glendale, CA (US); Rebecca K. Gottlieb, Culver City, CA (US); Benyamin Grosman, Winnetka, CA (US); Anirban Roy, Agoura Hills, CA (US); Neha J. Parikh, West Hills, CA (US); Ohad Cohen, Kiryat Uno (IL)

(73) Assignee: MEDTRONIC MINIMED, INC., Northridge, CA (US)

( * ) Notice: Subject to any disclaimer, the term of this patent is extended or adjusted under 35 U.S.C. 154(b) by 222 days.

(21) Appl. No.: 17/394,121

(22) Filed: Aug. 4, 2021

(65) Prior Publication Data
US 2021/0361866 A1   Nov. 25, 2021

Related U.S. Application Data

(63) Continuation of application No. 15/410,611, filed on Jan. 19, 2017, now Pat. No. 11,097,051.
(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61M 5/14244* (2013.01);
(Continued)

(58) Field of Classification Search
CPC .............. A61M 5/003; A61M 5/14244; A61M 5/14248; A61M 5/1723;
(Continued)

(56) References Cited

U.S. PATENT DOCUMENTS 3,631,847 A   1/1972   Hobbs, II
4,212,738 A   7/1980   Henne
(Continued)

FOREIGN PATENT DOCUMENTS

CA   3040537 A1   5/2018
CN   109891510 A   6/2019
(Continued)

OTHER PUBLICATIONS

International Preliminary Report on Patentability dated May 16, 2019 in Application No. PCT/US2017/059805.
(Continued)

*Primary Examiner* — Kami A Bosworth
(74) *Attorney, Agent, or Firm* — Weaver Austin Villeneuve & Sampson LLP

(57) ABSTRACT

Disclosed herein are techniques related to management of insufficient hypoglycemia response. In some embodiments, the techniques may involve obtaining an amount of insulin remaining in a body of a patient. The techniques may involve also obtaining a quantity of insulin needed by the patient within a future time period. Additionally, the techniques may involve identifying a condition in which the patient's glucose level will continue to decrease during the future time period despite suspension of basal insulin dosage delivery. The condition may be identified based on determining that the amount of insulin remaining in the body is greater than the quantity of insulin needed by the patient within the future time period. Furthermore, the techniques may involve, responsive to identifying the condition, causing performance of an action for preventing the patient's glucose level from falling into a hypoglycemic range in combination with the suspension of basal insulin dosage delivery.

12 Claims, 11 Drawing Sheets

Related U.S. Application Data

(60) Provisional application No. 62/417,843, filed on Nov. 4, 2016.

(51) Int. Cl.
  *A61M 5/142* (2006.01)
  *G16H 20/17* (2018.01)
  *G16H 40/63* (2018.01)
  *G16H 50/20* (2018.01)
  *G16H 50/50* (2018.01)

(52) U.S. Cl.
  CPC ............ *G16H 20/17* (2018.01); *G16H 40/63* (2018.01); *G16H 50/20* (2018.01); *G16H 50/50* (2018.01); *A61M 2005/14208* (2013.01); *A61M 2205/50* (2013.01); *A61M 2205/581* (2013.01); *A61M 2205/583* (2013.01)

(58) Field of Classification Search
  CPC .......... A61M 2005/14208; A61M 2005/1726; A61M 2205/3303; A61M 2230/005; A61M 2230/201; G16H 20/17; G16H 40/60; G16H 40/63; G16H 40/67
  See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Coleman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tackund et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |

(56) References Cited

U.S. PATENT DOCUMENTS

| | | |
|---|---|---|
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,833,157 B2 | 11/2010 | Gottlieb et al. |
| 11,097,051 B2 | 8/2021 | Wu et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0014785 A1 | 4/2004 | Holker et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0173406 A1 | 8/2006 | Hayes et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088271 A1 | 4/2007 | Richards |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2011/0313390 A1 | 12/2011 | Roy et al. |
| 2014/0039383 A1 | 2/2014 | Dobbles et al. |
| 2014/0221966 A1 | 8/2014 | Buckingham et al. |
| 2015/0157793 A1 | 6/2015 | Kovelman |
| 2015/0157796 A1 | 6/2015 | Dejournett |
| 2016/0228641 A1 | 8/2016 | Gescheit et al. |
| 2018/0055452 A1 | 3/2018 | Breton |
| 2018/0126073 A1 | 5/2018 | Wu et al. |

FOREIGN PATENT DOCUMENTS

| | | |
|---|---|---|
| DE | 4329229 | 3/1995 |
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| EP | 3535758 A1 | 9/2019 |
| GB | 2218831 | 11/1989 |
| WO | 96/20745 | 7/1996 |
| WO | 96/36389 | 11/1996 |
| WO | 96/37246 A1 | 11/1996 |
| WO | 97/21456 | 6/1997 |
| WO | 98/20439 | 5/1998 |
| WO | 98/24358 | 6/1998 |
| WO | 98/42407 | 10/1998 |
| WO | 98/49659 | 11/1998 |
| WO | 98/59487 | 12/1998 |
| WO | 99/08183 | 2/1999 |
| WO | 99/10801 | 3/1999 |
| WO | 99/18532 | 4/1999 |
| WO | 99/22236 | 5/1999 |
| WO | 00/10628 | 3/2000 |
| WO | 00/19887 | 4/2000 |
| WO | 00/48112 | 8/2000 |
| WO | 02/058537 A2 | 8/2002 |
| WO | 03/001329 | 1/2003 |
| WO | 03/094090 | 11/2003 |
| WO | 2005/065538 A2 | 7/2005 |
| WO | 2018085600 A1 | 5/2018 |

OTHER PUBLICATIONS

International Search Report and Written Opinion dated Jan. 25, 2018 in PCT Application No. PCT/US2017/059805.

U.S. Advisory Action dated Aug. 4, 2020, in U.S. Appl. No. 15/410,611.

(56) References Cited

OTHER PUBLICATIONS

U.S. Final Office Action dated Aug. 29, 2019, in U.S. Appl. No. 15/410,611.
U.S. Final Office Action dated Feb. 23, 2021, in U.S. Appl. No. 15/410,611.
U.S. Final Office Action dated May 19, 2020, in U.S. Appl. No. 15/410,611.
U.S. Non-Final Office Action dated Apr. 2, 2019, in U.S. Appl. No. 15/410,611.
U.S. Non-Final Office Action dated Feb. 10, 2020, in U.S. Appl. No. 15/410,611.
U.S. Non-Final Office Action dated Sep. 15, 2020, in U.S. Appl. No. 15/410,611.
U.S. Notice of Allowance dated Apr. 26, 2021, in U.S. Appl. No. 15/410,611.
U.S. Restriction Requirement dated Jan. 14, 2019, in U.S. Appl. No. 15/410,611.
Response to Examiner's Requisition dated Dec. 13, 2021, from counterpart Canadian Application No. 3040537, filed Mar. 30, 2022, 23 pp.
PCT Search Report (PCT/US02/03299), WO, Oct. 31, 2002, Medtronic MiniMed, Inc.
(Animas Corporation, 1999). Animas . . . bringing new life to insulin therapy. (Applicant points out, in accordance with MPEP 609.04(a), that the year of publication, 1999, is sufficiently earlier than the effective U.S. filing date, so that the particular month of publication is not in issue.
(Intensive Diabetes Management, 1995). Insulin Infusion Pump Therapy. pp. 66-78. (Applicant points out, in accordance with MPEP 609.04(a), that the year of publication, 1995, is sufficiently earlier than the effective U.S. filing date, so that the particular month of publication is not in issue).
(Medtronic MiniMed, 2002). Medtronic MiniMed Meal Bolus Calculator and Correction Bolus Calculator. International Version. (Applicant points out, in accordance with MPEP 609.04(a), that the year of publication, 2002, is sufficiently earlier than the effective U.S. filing date, so that the particular month of publication is not in issue).
(Medtronic MiniMed, 2002). The 508 Insulin Pump A Tradition of Excellence. (Applicant points out, in accordance with MPEP 609.04(a), that the year of publication, 2002, is sufficiently earlier than the effective U.S. filing date, so that the particular month of publication is not in issue).
(MiniMed Inc., 1999). Insulin Pump Comparison/Pump Therapy Will Change Your Life. (Applicant points out, in accordance with MPEP 609.04(a), that the year of publication, 1999, is sufficiently earlier than the effective U.S. filing date, so that the particular month of publication is not in issue).
(MiniMed Inc., 1999). MiniMed 508 Flipchart Guide to Insulin Pump Therapy. (Applicant points out, in accordance with MPEP 609.04(a), that the year of publication, 1999, is sufficiently earlier than the effective U.S. filing date, so that the particular month of publication is not in issue).
(MiniMed Inc., 2000). MiniMed® Now [I] Can Meal Bolus Calculator / MiniMed® Now [I] Can Correction Bolus Calculator. (Applicant points out, in accordance with MPEP 609.04(a), that the year of publication, 2000, is sufficiently earlier than the effective U.S. filing date, so that the particular month of publication is not in issue).
(MiniMed Inc., 2000). Now [I] Can MiniMed Diabetes Management. (Applicant points out, in accordance with MPEP 609.04(a), that the year of publication, 2000, is sufficiently earlier than the effective U.S. filing date, so that the particular month of publication is not in issue).
(MiniMed Inc., 2000). Now [I] Can MiniMed Pump Therapy. (Applicant points out, in accordance with MPEP 609.04(a), that the year of publication, 2000, is sufficiently earlier than the effective U.S. filing date, so that the particular month of publication is not in issue).
(MiniMed International, 1998). MiniMed 507C Insulin Pump For those who appreciate the difference. (Applicant points out, in accordance with MPEP 609.04(a), that the year of publication, 1998, is sufficiently earlier than the effective U.S. filing date, so that the particular month of publication is not in issue).
(MiniMed Technologies, 1994). MiniMed™ Dosage Calculator Initial Meal Bolus Guidelines/MiniMedTM Dosage Calculator Initial Basal Rate Guidelines Percentage Method. 4 pages. (Applicant points out, in accordance with MPEP 609.04(a), that the year of publication, 1994, is sufficiently earlier than the effective U.S. filing date, so that the particular month of publication is not in issue).
(MiniMed Technologies, 1994). MiniMed 506 Insulin Pump User's Guide. (Applicant points out, in accordance with MPEP 609.04(a), that the year of publication, 1994, is sufficiently earlier than the effective U.S. filing date, so that the particular month of publication is not in issue).
(MiniMed, 1996). FAQ: The Practical Things . . . pp. 1-4. Retrieved on Sep. 16, 2003 from the World Wide Web: http://web.archive.org/web/19961111054546/www.minimed.com/files/faq pract.htm.
(MiniMed, 1996). MiniMed™ 507 Insulin Pump User's Guide. (Applicant points out, in accordance with MPEP 609.04(a), that the year of publication, 1996, is sufficiently earlier than the effective U.S. filing date, so that the particular month of publication is not in issue).
(MiniMed, 1996). The MiniMed 506. 7 pages. Retrieved on Sep. 16, 2003 from the World Wide Web: http://web.archive.org/web/19961111 054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www. minimed.com/files/mmn075.htm.
(MiniMed, 1997). MiniMed™ 507 Insulin Pump User's Guide. (Applicant points out, in accordance with MPEP 609.04(a), that the year of publication, 1997, is sufficiently earlier than the effective U.S. filing date, so that the particular month of publication is not in issue).
(MiniMed, 1997). Wanted: a Few Good Belt Clips! 1 page. Retrieved on Sep. 16, 2003 from the World Wide Web: http://web. archive.org/web/19970124234559/www. minimed.com/files/mmn002. htm.
(MiniMed, 1998). MiniMed 507C Insulin Pump User's Guide. (Applicant points out, in accordance with MPEP 609.04(a), that the year of publication, 1998, is sufficiently earlier than the effective U.S. filing date, so that the particular month of publication is not in issue).
(MiniMed, 2000). MiniMed® 508 User's Guide. (Applicant points out, in accordance with MPEP 609.04(a), that the year of publication, 2000, is sufficiently earlier than the effective U.S. filing date, so that the particular month of publication is not in issue).
Abel et al., "Experience with an implantable glucose sensor as a prerequisite of an artificial beta cell," Biomed. Biochim. Acta 43 (1984) 5, pp. 577-584. (Applicant points out, in accordance with MPEP 609.04(a), that the year of publication, 1984, is sufficiently earlier than the effective U.S. filing date, so that the particular month of publication is not in issue).
Bindra et al., "Design and in Vitro Studies of a Needle-Type Glucose Sensor for a Subcutaneous Monitoring," American Chemistry Society, vol. 63, No. 17, Sep. 1991, 63, pp. 1692-1696.
Bode et al., "Reduction in Severe Hypoglycemia with Long-Term Continuous Subcutaneous Insulin Infusion in Type I Diabetes," Diabetes Care, vol. 19, No. 4, Apr. 1996, pp. 324-327.
Boguslavsky et al., "Applications of redox polymers in biosensors," Sold State Ionics, vol. 60, Mar. 1993, pp. 189-197.
Boland E (Jan. 1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28. (Applicant points out, in accordance with MPEP 609.04(a), that the year of publication, 1992, is sufficiently earlier than the effective U.S. filing date, so that the particular month of publication is not in issue).
Brackenridge, B Petal. (1995). Counting Carbohydrates How to Zero in on Good Control. MiniMed Technologies Inc. (Applicant points out, in accordance with MPEP 609.04(a), that the year of

(56) References Cited

OTHER PUBLICATIONS publication, 1995, is sufficiently earlier than the effective U.S. filing date, so that the particular month of publication is not in issue).
Disetronic H-TRON® plus Quick Start Manual. (no date).
Disetronic H-TRON® plus Reference Manual. (no date).
Disetronic My Choice H-TRON plus Insulin Pump Reference Manual. (no date).
Disetronic My Choice™ D-TRON™ Insulin Pump Reference Manual. (no date).
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138. (Applicant points out, in accordance with MPEP 609.04(a), that the year of publication, 1994, is sufficiently earlier than the effective U.S. filing date, so that the particular month of publication is not in issue).
Geise et al., "Electropolymerized 1,3-diaminobenzene for the construction of a 1,1'-dimethylferrocene mediated glucose biosensor," Analytica Chimica Acta, vol. 281, No. 3, Sep. 1993, pp. 467-473.
Gernet et al., "A Planar Glucose Enzyme Electrode," Sensors and Actuators, vol. 17, May 1989, pp. 537-540.
Gernet et al., "Fabrication and Characterization of a Planar Electromechanical Cell and its Application as a Glucose Sensor," Sensors and Actuators, vol. 18, Jun. 1989, pp. 59-70.
Gorton et al., "Amperometric Biosensors Based on an Apparent Direct Electron Transfer Between Electrodes and Immobilized Peroxdiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A, et al., "Two-Dimensional Enzyme Electrode Sensor for Glucose," Analytical Chemistry, vol. 57, No. 5, Oct. 1985, pp. 2351-2357.
Gregg, Brian A., et al., "Cross-Linked Redox Gels Containing Glucose Oxidase for Amperometric Biosensor Applications," Analytical Chemistry, vol. 62, No. 3, Feb. 1990, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, Jul. 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Hirsch et al., "Intensive Insulin Therapy for Treatment of Type I Diabetes," Diabetes Care, vol. 13, No. 12, Dec. 1990, pp. 1265-1283.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714. (Applicant points out, in accordance with MPEP 609.04(a), that the year of publication, 1992, is sufficiently earlier than the effective U.S. filing date, so that the particular month of publication is not in issue).
Jonsson, G., et al., "An Electromechanical Sensor for Hydrogen Peroxide Based on Peroxidase Adsorbed on a Spectrographic Graphite Electrode," Electroanalysis, vol. 1, No. 5, Sep. 1989, pp. 465-468.
Kanapieniene, J. J., et al., "Miniature Glucose Biosensor with Extended Linearity," Sensors and Actuators, B: Chemical, vol. 10, No. 1, Dec. 1992, pp. 37-40.
Kawamori, Ryuzo, et al., "Perfect Normalization of Excessive Glucagon Responses to Intravenous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors, vol. 4, No. 1, 1988, pp. 41-52. (Applicant points out, in accordance with MPEP 609.04(a), that the year of publication, 1988, is sufficiently earlier than the effective U.S. filing date, so that the particular month of publication is not in issue).
Koudelka, M., et al., "In-vivo Behaviour of Hypodermically Implanted Microfabricated Glucose Sensors," Biosensors & Bioelectronics, vol. 6, 1991, pp. 31-36. (Applicant points out, in accordance with MPEP 609.04(a), that the year of publication, 1991, is sufficiently earlier than the effective U.S. filing date, so that the particular month of publication is not in issue).
Koudelka, M., et al., "Planar Amperometric Enzyme-Based Glucose Microelectrode," Sensors & Actuators, vol. 18, Jun. 1989, pp. 157-165.
Kulkarni K et al. (Jan. 1999). Carbohydrate Counting A Primer for Insulin Pump Users to Zero in on Good Control. MiniMed Inc.
Marcus et al., "Insulin Pump Therapy Acceptable Alternative to Injection Therapy," Postgraduate Medicine, vol. 99, No. 3, Mar. 1996, pp. 125-142.
Mastrototaro et al., "An electroenzymatic glucose sensor fabricated on a flexible substrate," Sensors & Actuators, B: Chemical; vol. 5, Aug. 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, vol. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annual International Conference of the IEEE Engineering in Medicine and Biology Society, vol. 12, No. 2, Nov. 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators, vol. 13, Feb. 1988, pp. 165-172.
Nishida, Kenro, et al., "Clinical applications of the wearable artificial endocrine pancreas with the newly designed needle-type glucose sensor," Elsevier Sciences B.V., 1994, pp. 353-358. (Applicant points out, in accordance with MPEP 609.04(a), that the year of publication, 1994, is sufficiently earlier than the effective U.S. filing date, so that the particular month of publication is not in issue).
Nishida, Kenro, et al., "Development of a ferrocene-mediated needle-type glucose sensor covered with newly designed biocompatible membrane, 2-methacryloyloxyethyl phosphorylcholine-co-n-butyl methacrylate," Medical Progress Through Technology, vol. 21, Apr. 1995, pp. 91-103.
Office Action from counterpart Canadian Application No. 3,040,537, dated Feb. 9, 2021, 4 pp.
Poitout, V., et al., "A glucose monitoring system for on line estimation in man of blood glucose concentration using a miniaturized glucose sensor implanted in the subcutaneous tissue and a wearable control unit," Diabetologia, vol. 36, Jul. 1991, pp. 658-663.
Reach, G., "A Method for Evaluating in vivo the Functional Characteristics of Glucose Sensors," Biosensors, vol. 2, 1986, pp. 211-220. (Applicant points out, in accordance with MPEP 609.04(a), that the year of publication, 1986, is sufficiently earlier than the effective U.S. filing date, so that the particular month of publication is not in issue).
Reed, J., "Living with Diabetes," Voice of the Diabetic, vol. 11, No. 3, Summer Edition 1996, pp. 1-38. (Applicant points out, in accordance with MPEP 609.04(a), that the year of publication, 1996, is sufficiently earlier than the effective U.S. filing date, so that the particular month of publication is not in issue).

(56) References Cited

OTHER PUBLICATIONS

Shaw, G. W., et al., "In vitro testing of a simply constructed, highly stable glucose sensor suitable for implantation in diabetic patients," Biosensors & Bioelectronics, vol. 6, 1991, pp. 401-406. (Applicant points out, in accordance with MPEP 609.04(a), that the year of publication, 1991, is sufficiently earlier than the effective U.S. filing date, so that the particular month of publication is not in issue).

Shichiri, M., "A Needle-Type Glucose Sensor—A Valuable Tool Not Only for a Self-Blood Glucose Monitoring but for a Wearable Artificial Pancreas," Life Support Systems Proceedings, XI Annual Meeting ESAO, Alpbach-Innsbruck, Austria, Sep. 1984, pp. 7-9.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20. (Applicant points out, in accordance with MPEP 609.04(a), that the year of publication, 1988, is sufficiently earlier than the effective U.S. filing date, so that the particular month of publication is not in issue).

Shichiri, M., et al., "Membrane design for extending the long-life of an implantable glucose sensor," Diab. Nutr. Metab., vol. 2, No. 4, 1989, pp. 309-313. (Applicant points out, in accordance with MPEP 609.04(a), that the year of publication, 1989, is sufficiently earlier than the effective U.S. filing date, so that the particular month of publication is not in issue).

Shichiri, Motoaki, et al., "An artificial endocrine pancreas—problems awaiting solution for long-term clinical applications of a glucose sensor," Frontiers Med. Bioi. Engng., 1991, vol. 3, No. 4, pp. 283-292. (Applicant points out, in accordance with MPEP 609.04(a), that the year of publication, 1991, is sufficiently earlier than the effective U.S. filing date, so that the particular month of publication is not in issue).

Shichiri, Motoaki, et al., "Closed-Loop Glycemic Control with a Wearable Artificial Endocrine Pancreas-Variations in Daily Insulin Requirements to Glycemic Response," Diabetes, vol. 33, Dec. 1984, pp. 1200-1202.

Shichiri, Motoaki, et al., "Glycaemic Control in a Pancreatectomized Dogs with a Wearable Artificial Endocrine Pancreas," Diabetologia, vol. 24, Mar. 1983, pp. 179-184.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn, Sep. 1984, vol. 26, pp. 359-370.

Shichiri, Motoaki, et al., "Wearable Artificial Endocrine Pancreas with Needle-Type Glucose Sensor." The Lancet, Nov. 20, 1982, pp. 1129-1131.

Shinkai, Seiji, "Molecular Recognition of Mono- and Disaccharides by Phenylboronic Acids in Solvent Extraction and as a Monolayer," J. Chern. Soc., Chern. Commun., vol. 15, Aug. 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Skyler J S (1989). Continuous Subcutaneous Insulin Infusion [CSII] With External Devices: Current Status. Update in Drug Delivery Systems, Chapter 13, pp. 163-183. Futura Publishing Company. (Applicant points out, in accordance with MPEP 609.04(a), that the year of publication, 1989, is sufficiently earlier than the effective U.S. filing date, so that the particular month of publication is not in issue).

Skyler J S et al. (1995). The Insulin Pump Therapy Book Insights from the Experts. MiniMed.Technologies. (Applicant points out, in accordance with MPEP 609.04(a), that the year of publication, 1995, is sufficiently earlier than the effective U.S. filing date, so that the particular month of publication is not in issue).

Sternberg, Robert, et al., "Study and Development of Multilayer Needle-type Enzyme-based Glucose Microsensors," Biosensors, vol. 4, Dec. 1988, pp. 27-40.

Strowig S M, "Initiation and Management of Insulin Pump Therapy," The Diabetes Educator, vol. 19, No. 1, Feb. 1993, pp. 50-60.

Tamiya, E., et al., "Micro Glucose Sensors using Electron Mediators Immobilized on a Polypyrrole-Modified Electrode," Sensors and Actuators, vol. 18, Jul. 1989, pp. 297-307.

Tsukagoshi, Kazuhiko, et al., "Specific Complexation with Mono- and Disaccharides that can be Detected by Circular Dichroism," J. Org. Chem., vol. 56, Jun. 1991, pp. 4089-4091.

Ubran, G., et al., "Miniaturized thin-film biosensors using covalently immobilized glucose oxidase," Biosensors & Bioelectronics, vol. 6, 1991, pp. 555-562. (Applicant points out, in accordance with MPEP 609.04(a), that the year of publication, 1991, is sufficiently earlier than the effective U.S. filing date, so that the particular month of publication is not in issue).

Urban, G., et al., "Miniaturized multi-enzyme biosensors integrated with pH sensors on flexible polymer carriers for in vivo applications," Biosensors & Bioelectronics, vol. 7, 1992, pp. 733-739. (Applicant points out, in accordance with MPEP 609.04(a), that the year of publication, 1992, is sufficiently earlier than the effective U.S. filing date, so that the particular month of publication is not in issue).

Velho, G., et al., "In vivo calibration of a subcutaneous glucose sensor for determination of subcutaneous glucose kinetics," Diab. Nutr Metab, vol. 3, 1988, pp. 227-233. (Applicant points out, in accordance with MPEP 609.04(a), that the year of publication, 1988, is sufficiently earlier than the effective U.S. filing date, so that the particular month of publication is not in issue).

Walsh J, et al. (1989). Pumping Insulin: The Art of Using an Insulin Pump. Published by MiniMed•Technologies. (Applicant points out, in accordance with MPEP 609.04(a), that the year of publication, 1989, is sufficiently earlier than the effective U.S. filing date, so that the particular month of publication is not in issue).

Wang, Joseph, et al., "Needle-Type Dual Microsensor for the Simultaneous Monitoring of Glucose and Insulin," Analytical Chemistry, vol. 73, Feb. 2001, pp. 844-847.

Yamasaki, Yoshimitsu, et al, "Direct Measurement of Whole Blood Glucose by a Needle-Type Sensor," Clinics Chimica Acta, vol. 180, Mar. 1989, pp. 93-98.

Yokoyama, K., "Integrated Biosensor for Glucose and Galactose," Analytica Chimica Acta, vol. 218, 1989, pp. 137-142. (Applicant points out, in accordance with MPEP 609.04(a), that the year of publication, 1989, is sufficiently earlier than the effective U.S. filing date, so that the particular month of publication is not in issue).

Response to Office Action from counterpart Canadian Application No. 3,040,537, dated Feb. 9, 2021, filed Jun. 4, 2021, 21 pp.

Prosecution History from U.S. Appl. No. 15/410,611, dated Jan. 14, 2019 through Apr. 26, 2021, 172 pp.

Office Action from counterpart Canadian Application No. 3,040,537 dated Dec. 13, 2021, 5 pp.

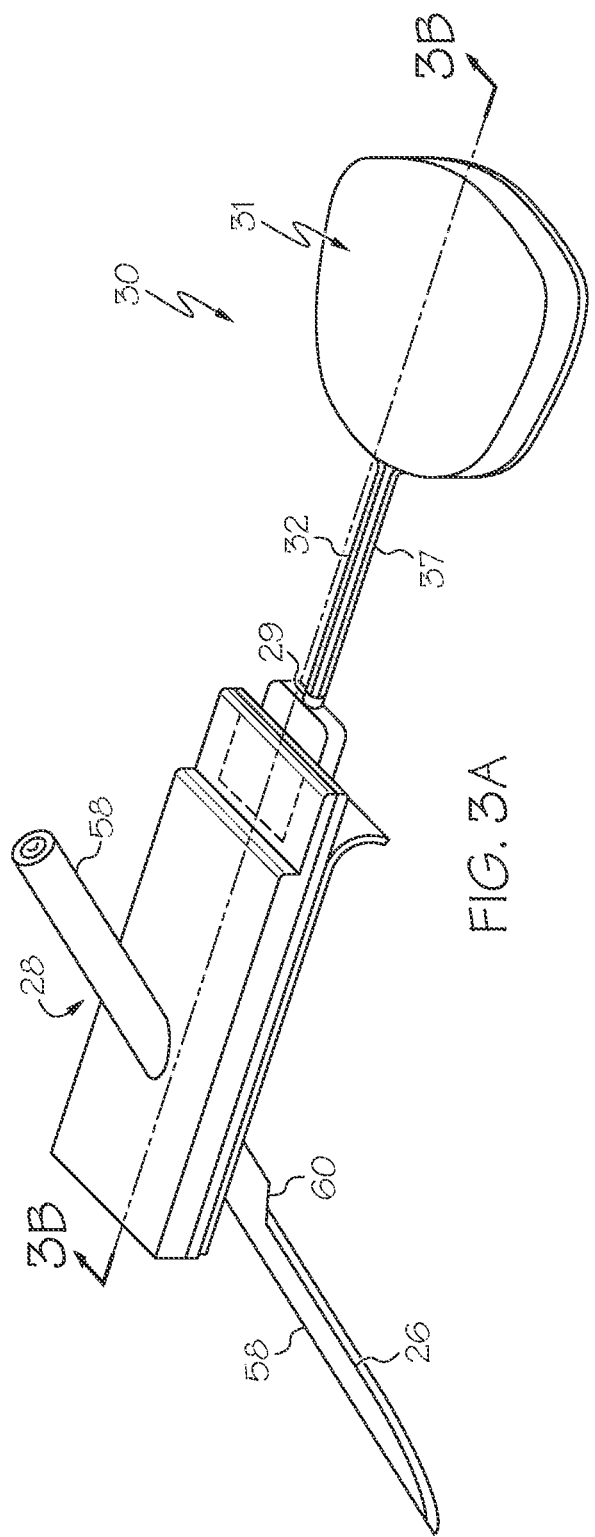
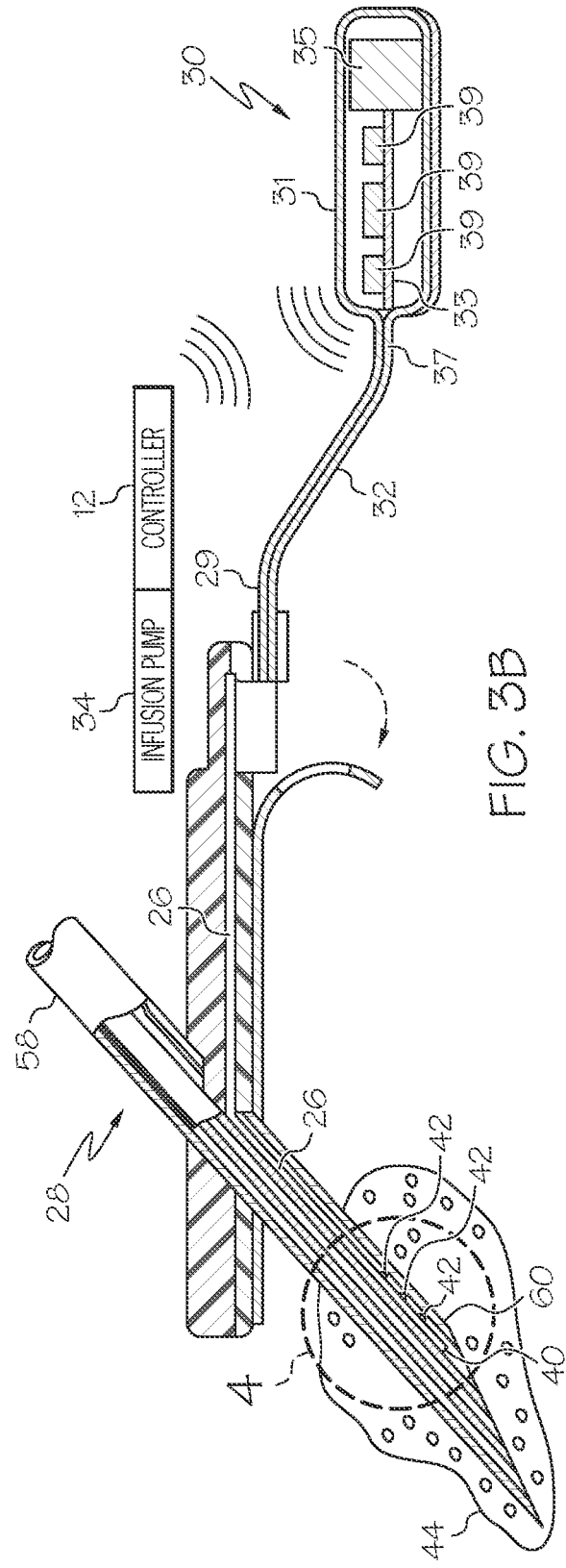

MANAGEMENT OF INSUFFICIENT HYPOGLYCEMIA RESPONSE

CROSS-REFERENCE TO RELATED APPLICATION

This application is a continuation of U.S. patent application Ser. No. 15/410,611, filed 19 Jan. 2017, and issued on 24 Aug. 2021 as U.S. Pat. No. 11,097,051, which claims the benefit of U.S. Provisional Patent Application No. 62/417,843, filed 4 Nov. 2016, the entire content of each of which is incorporated herein by reference.

TECHNICAL FIELD

Subject matter disclosed herein relates to management of insufficient hypoglycemia response.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded glucose sensor in real-time. Closed-loop infusion pump systems may also employ the delivery of glucose and/or glucagon, in addition to the delivery of insulin, for controlling blood-glucose levels of a patient (e.g., in a hypoglycemic context).

BRIEF SUMMARY

Disclosed herein are techniques related to management of insufficient hypoglycemia response. The techniques may be practiced using a processor-implemented method; a system comprising one or more processors and one or more processor-readable storage media; and/or one or more non-transitory processor-readable storage media.

In some embodiments, the techniques may involve obtaining an amount of insulin remaining in a body of a patient. The techniques may involve also obtaining a quantity of insulin needed by the patient within a future time period. Additionally, the techniques may involve identifying a condition in which the patient's glucose level will continue to decrease during the future time period despite suspension of basal insulin dosage delivery. The condition may be identified based on determining that the amount of insulin remaining in the body is greater than the quantity of insulin needed by the patient within the future time period. Furthermore, the techniques may involve, responsive to identifying the condition, causing performance of an action for preventing the patient's glucose level from falling into a hypoglycemic range in combination with the suspension of basal insulin dosage delivery.

In some embodiments, the techniques may further involve, prior to identifying the condition, causing a medication delivery device to suspend basal insulin dosage delivery based on identifying a glucose trend in the patient toward the hypoglycemic range. Identifying the glucose trend in the patient may involve obtaining a plurality of glucose values, calculating a glucose trend value based on computing the derivative of the plurality of glucose values, and comparing the glucose trend value to a hypoglycemia threshold. In some embodiments, the amount of insulin remaining in the body is represented as an insulin-on-board (IOB) value corresponding to a quantity of insulin remaining in the patient following delivery of a bolus of insulin. Additionally or alternatively, the quantity of insulin needed by the patient is calculated based on a total daily dose (TDD) value, which corresponds to an estimated quantity of insulin to be delivered to the patient in a twenty-four hour period. The TDD value may be scaled by a factor to result in a value that is less than the TDD value. In some embodiments, causing performance of the action involves communicating a command to a medication delivery device. In some embodiments, the action involves delivering glucagon to the patient. In some embodiments, the action involves presenting a recommendation to ingest a substance for increasing the patient's glucose level.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3A is a perspective view of a glucose sensor system for use in accordance with an embodiment;

FIG. 3B is a side cross-sectional view of the glucose sensor system of FIG. 3A for an embodiment;

DETAILED DESCRIPTION

Figure 1:
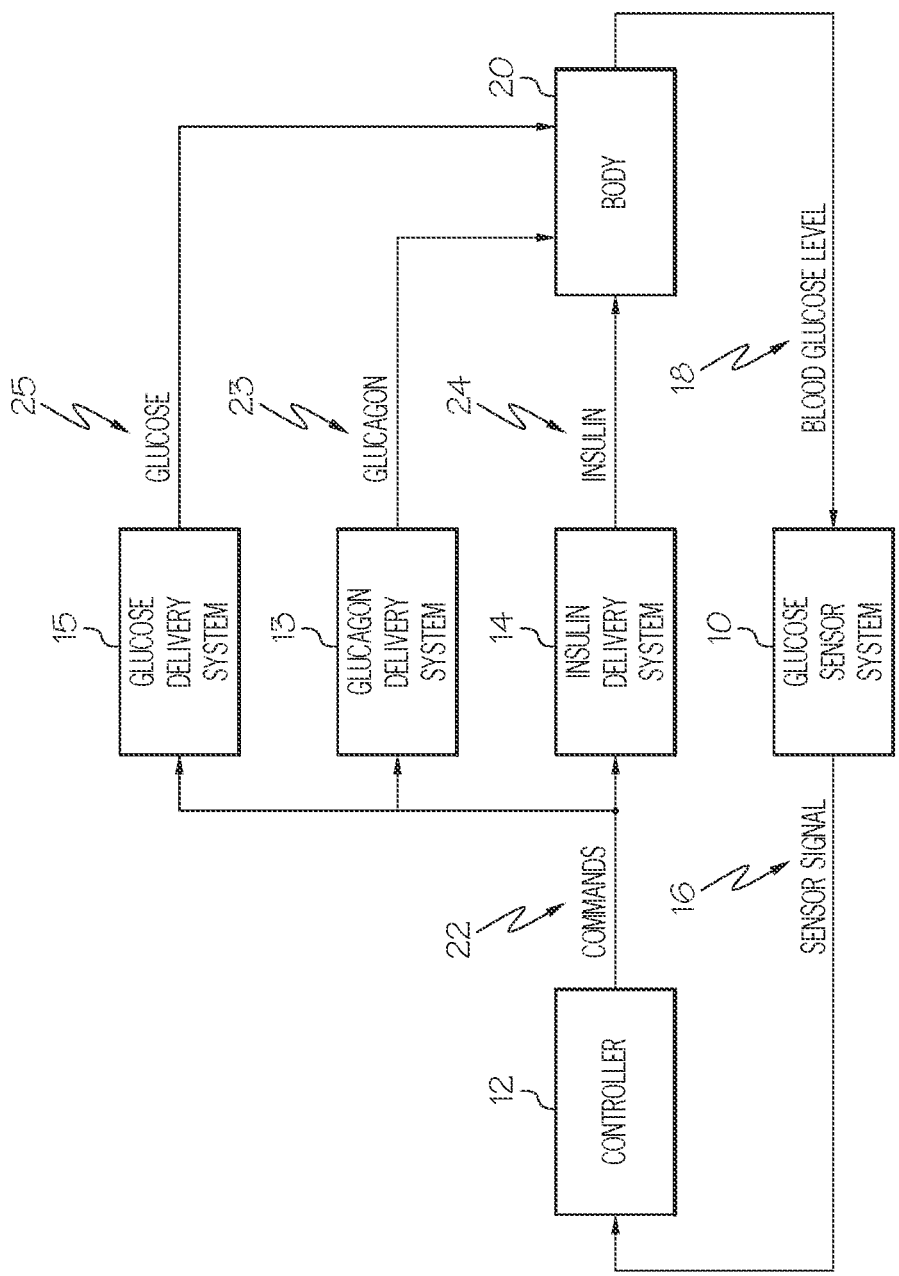
FIG. 1 is a block diagram of a closed loop glucose control system in accordance with an embodiment.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter presented herein relates to apparatus and methods for predicting an insufficient response, by an insulin delivery pump, to a hypoglycemic event. An insulin delivery pump normally operates to: (i) provide a continuous delivery of basal insulin to a user of the pump, and (ii) provide a bolus (i.e., a single dose of a drug or other medicinal preparation given all at once) of insulin, on an as-needed basis. Under normal operation, the insulin delivery pump detects anticipated hypoglycemic events and responds by suspending the continuous basal insulin delivery, in an attempt to prevent an upcoming hypoglycemic event. In certain circumstances, such suspension of basal insulin delivery is insufficient to prevent the hypoglycemic event. In this scenario, the insulin delivery pump can first predict the anticipated insufficient response, and second perform an action based on the anticipated insufficient response. Such actions may include presenting an alert, providing information for patient education, and/or providing a glucagon injection via the insulin delivery pump.

Certain terminologies are used with regard to the various embodiments of the present disclosure. A glucose trend is the rate of change for a series of blood glucose values, acquired over a period of time, from a single patient or user of an sensor augmented insulin delivery pump. Hypoglycemia is a low level of glucose in the bloodstream of the patient or user of the insulin delivery pump, and may be generally associated with blood glucose values below 70 milligrams per deciliter (mg/dL). An insulin on board (IOB) value is descriptive of the residual insulin activity following a bolus of insulin provided by the insulin delivery pump. A total daily dose (TDD) value is a quantity of insulin required by the user in a twenty-four (24) hour period. A missed hypoglycemic event is an occurrence of a time period of hypoglycemia that is not prevented, avoided, or corrected by suspension of a continuous delivery of basal insulin.

In an exemplary glucose control system environment, blood-glucose measurements may be employed in a closed loop infusion system for regulating a rate of fluid infusion into a body. In particular embodiments, a control system may be adapted to regulate a rate of insulin, glucagon, and/or glucose infusion into a body of a patient based, at least in part, on a glucose concentration measurement taken from a body (e.g., from a glucose sensor and/or metered blood glucose measurement). In certain implementations, such a system may be designed to model a pancreatic beta cell (β-cell). Here, such a system may enable a patient to control an infusion device for releasing insulin, glucagon or glucose into the patient's body for effective blood glucose management. Here, such a system may be adapted to control infusion of insulin and/or glucagon so as to control/maintain a patient's blood glucose within a target range, thus reducing the risk that a patient's blood glucose level transitions to dangerous extreme levels in the absence of patient action.

According to certain embodiments, examples of closed-loop systems as described herein may be implemented in a hospital environment to monitor and/or control levels of glucose in a patient. Alternatively, according to certain embodiments, examples of closed-loop systems as described herein may be implemented in non-hospital environments to monitor and/or control levels of glucose in a patient. Here, a patient or other non-medical professional may be responsible for interacting with a closed-loop system.

To maintain healthy glucose levels, a person with type 1 diabetes may manage their glycemia by monitoring blood glucose levels, controlling diet, exercise, and self-administering appropriate amounts of insulin at appropriate times. Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

In a particular embodiment of a closed-loop system, such a system may be adapted to control infusion of insulin and/or glucagon so as to control/maintain a patient's blood glucose within a target range, thus reducing the risk that a patient's blood glucose level transition to dangerous extreme levels. Again, such a mechanism may reduce the risk of hypoglycemia and hyperglycemia if a patient, non-medical professional or medical professional is not fully attentive to providing inputs to the system for effective glycemic management.

According to an embodiment, depending on a patient's particular physiology, a target or set-point glucose level may be established. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dL, which is in the normal glycemic range. Alternatively, target or set-point glucose level may be fixed at 120 mg/dL. In yet another alternative, a target or set-point blood glucose concentration may vary over time depending on particular patient conditions. It should be understood, however, that these are merely examples of a target or set-point blood glucose concentration, and claimed subject matter is not limited in this respect.

According to an embodiment, a closed-loop system may be employed to maintain a patient's glucose level in a range about a predetermined set-point or target level as described in U.S. patent application Ser. No. 12/820,944, filed on Jun. 22, 2010, and assigned to the assignee of claimed subject matter. Here, insulin may be infused to the patient at a predetermined basal rate while the patient's glucose level is within the predetermined range. If the glucose level escapes that range, a different infusion rate may be applied based, at least in part, on the predetermined set-point or target level. For example, if the patient's glucose level exceeds the range, an insulin infusion rate may be increased. In another example, if the patient's glucose level falls below a particular level, an insulin infusion rate may be reduced from the predetermined basal rate. Of course, these are merely examples of how the insulin infusion rate may be changed if a patient's glucose level escapes a particular range, and claimed subject matter is not limited in this respect.

By maintaining a predetermined basal insulin infusion rate while the glucose level is within a target range, extreme glycemic variations may be reduced or avoided altogether. This may provide a patient with improved glycemic control in circumstances in which they would otherwise be exposed to undesirable extremes of glycemia. Here, while such a patient may remain in control of insulin infusion decisions, particular embodiments may respond automatically in the absence of particular patient action (e.g., forgetting to bolus insulin to cover a meal) to prevent blood glucose from reaching extreme levels.

A controller may employ any one of several control techniques for computing determining commands for a pump in attempt to maintain a patient's observed blood glucose concentration within a target range. For example, a controller may employ a proportional-integral-derivative (PID) control algorithm in conjunction with controlling a patient's blood glucose level within a particular range as described in U.S. patent application Ser. No. 12/820,944, filed on Jun. 22, 2010, and assigned to the assignee of claimed subject matter. Here, such a PID algorithm may, at least in part, predict a level of blood glucose in a patient at some set time in the future and, based on such a prediction, compute commands to be provided to an infusion pump. While such a PID algorithm may provide an effective technique for maintaining a patient's blood glucose within a target range, a PID algorithm may not fully consider health risks of a blood glucose level being outside of a target range from time to time.

Briefly, according to an embodiment, a predicted blood glucose level of a patient based, at least in part, on past blood glucose measurements and control signals to be applied to at least one infusion pump. A cost expression is determined based, at least in part, on the predicted blood glucose level. The control signals to be applied to the at least one infusion pump may then be affected so as to achieve a cost value according to said cost expression. In one particular implementation, that cost expression is determined based, at least in part, on a predicted duration that that the blood glucose is to be outside of a target range over some interval in the future. Accordingly, the control signals applied to the at least on infusion pump may be responsive to risks associated with the patient's blood glucose level being outside of the target range.

As pointed out above, insulin infusion therapy may be controlled, at least in part, by techniques for predicting a patient's blood glucose level or glycemic state at some point or time in the future (e.g., using a PID algorithm as discussed above). In this context, a "glycemic state" may be determined based on one or more factors such as, for example, a blood glucose concentration. Algorithms may receive measurements or observations of a patient's blood glucose concentration from, for example, a continuous blood glucose monitoring device processing signals from a blood-glucose sensor inserted into subcutaneous tissue. However, merely predicting a blood glucose level at some time in the future may have limited utility in applying a therapy to a patient. For example, systems that predict a blood glucose concentration at some time in the future may merely provide a single blood glucose level prediction for a single instance in the future, and may not fully characterize a patient's glycemic state, or transitions from an initial glycemic state to a possible future glycemic state, for the purpose of applying an appropriate therapy.

In another implementation, insulin infusion therapy may be affected or controlled by a prediction of a duration of time until a patient's current glycemic state or blood glucose level is to reach a target blood glucose concentration or glycemic state. Among other factors, this predicted duration may be based, at least in part, on observations of the patient's current blood glucose level according to signals received from a blood-glucose sensor. This predicted duration may then be used for determining how the patient's therapy may be altered by, for example, changing a rate of insulin infusion.

Predicting a duration of time until a patient is to reach a particular blood glucose level starting from an initial state may enable techniques for characterizing a patient's glycemic state that may not be possible with predicting the patient's blood-glucose level in the future alone. Additionally, a predicted time until a patient reaches a particular glycemic state may enable an enhanced ability to for closed-loop insulin infusion systems.

Turning now to the figures, FIG. 1 is a block diagram of an example closed-loop glucose control system in accordance with an embodiment. Particular embodiments may include a glucose sensor system 10, a controller 12, an insulin delivery system 14, a glucagon delivery system 13, and a glucose delivery system 15, as shown in FIG. 1. In certain exemplary embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and provide glucose 25 into body 20 in response to commands 22.

Glucose sensor system 10 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using, e.g., a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such observations or measurements, and that other techniques, such as measuring blood glucose inform observations of other body fluids (e.g., observations of the presence of glucose in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable, a wire, a fiber optic line, RF, IR, or ultrasonic transmitters and receivers, combinations thereof, and/or the like instead of electrical traces, just to name a few examples.

Figure 2:
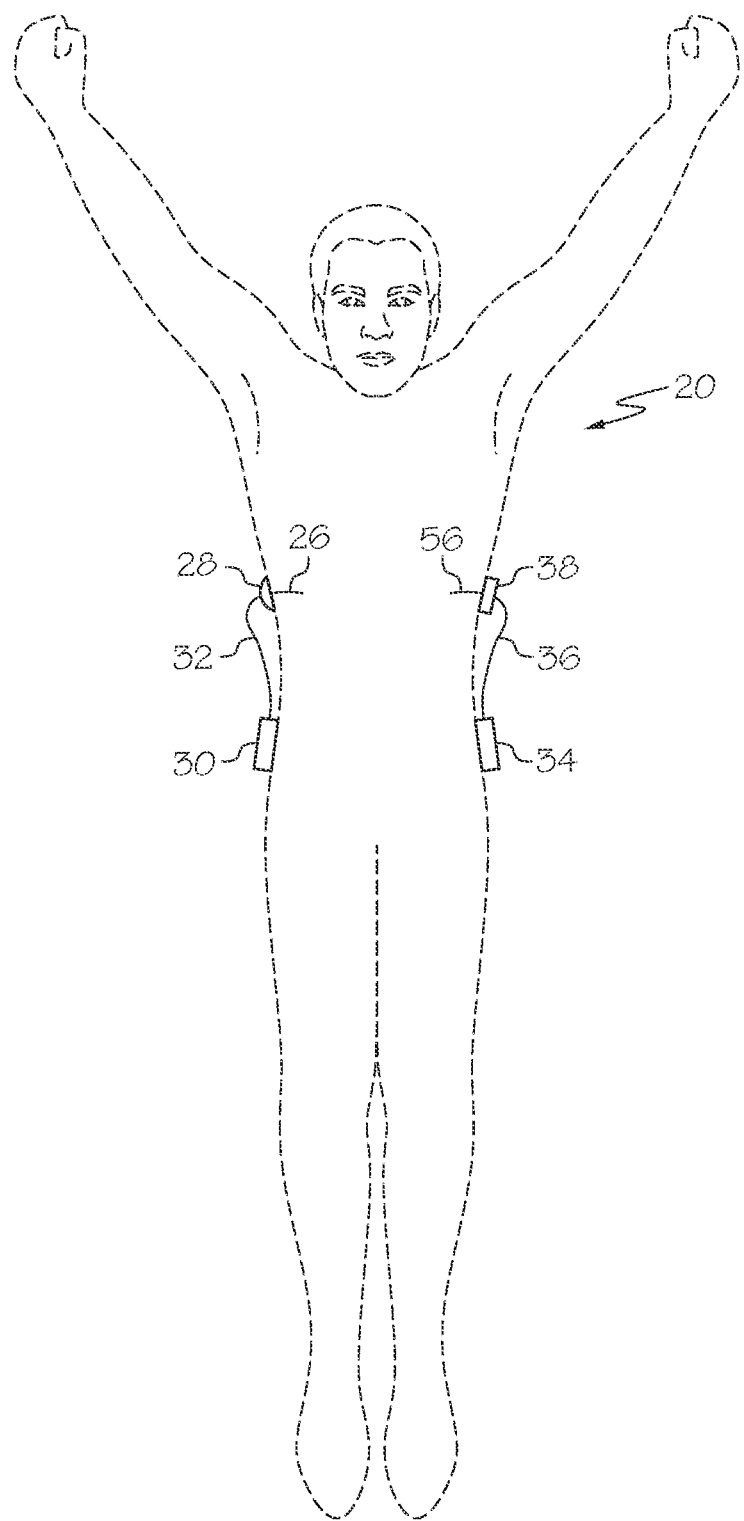
FIG. 2 is a front view of closed loop hardware located on a body in accordance with an embodiment.
Figure 3C:
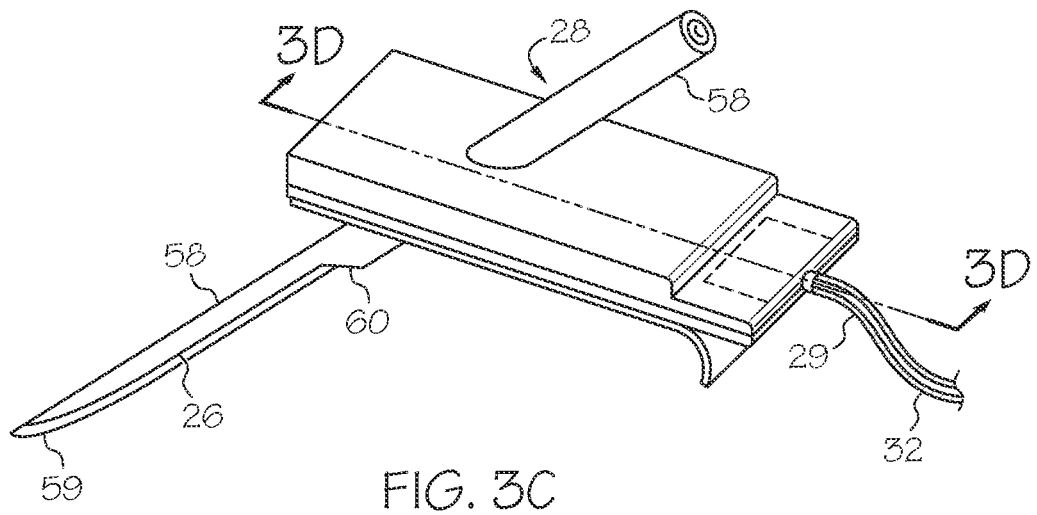
FIG. 3C is a perspective view of a sensor set of a glucose sensor system of FIG. 3A for an embodiment.
Figure 3D:
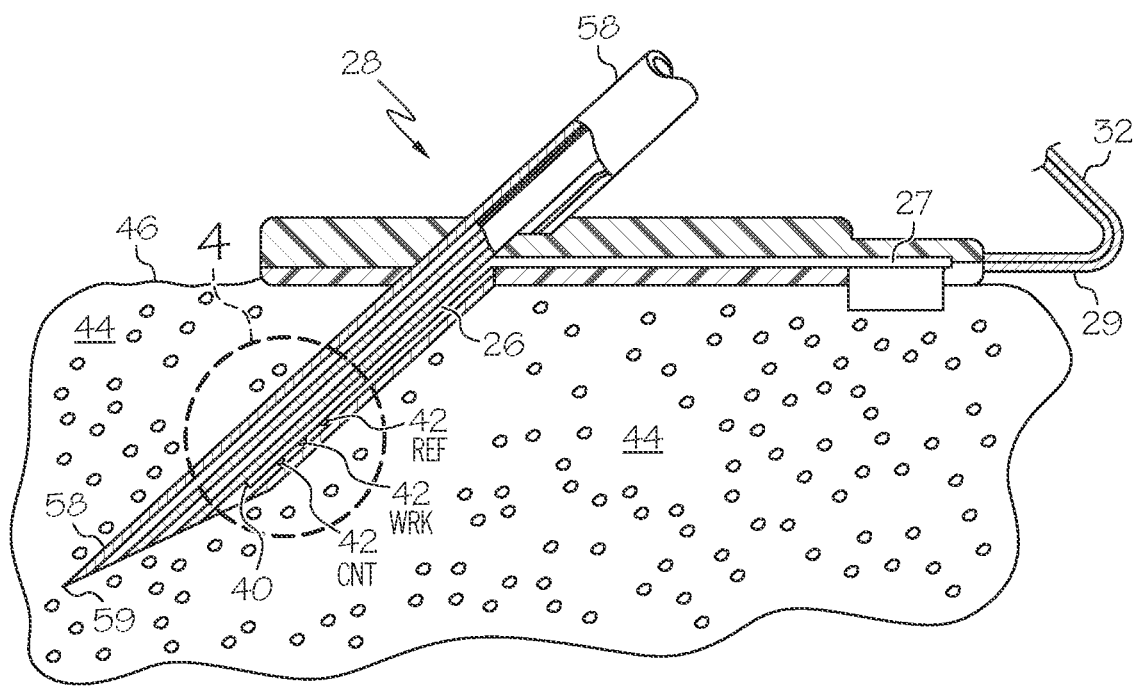
FIG. 3D is a side cross-sectional view of a sensor set of FIG. 3C for an embodiment.
Figure 4:
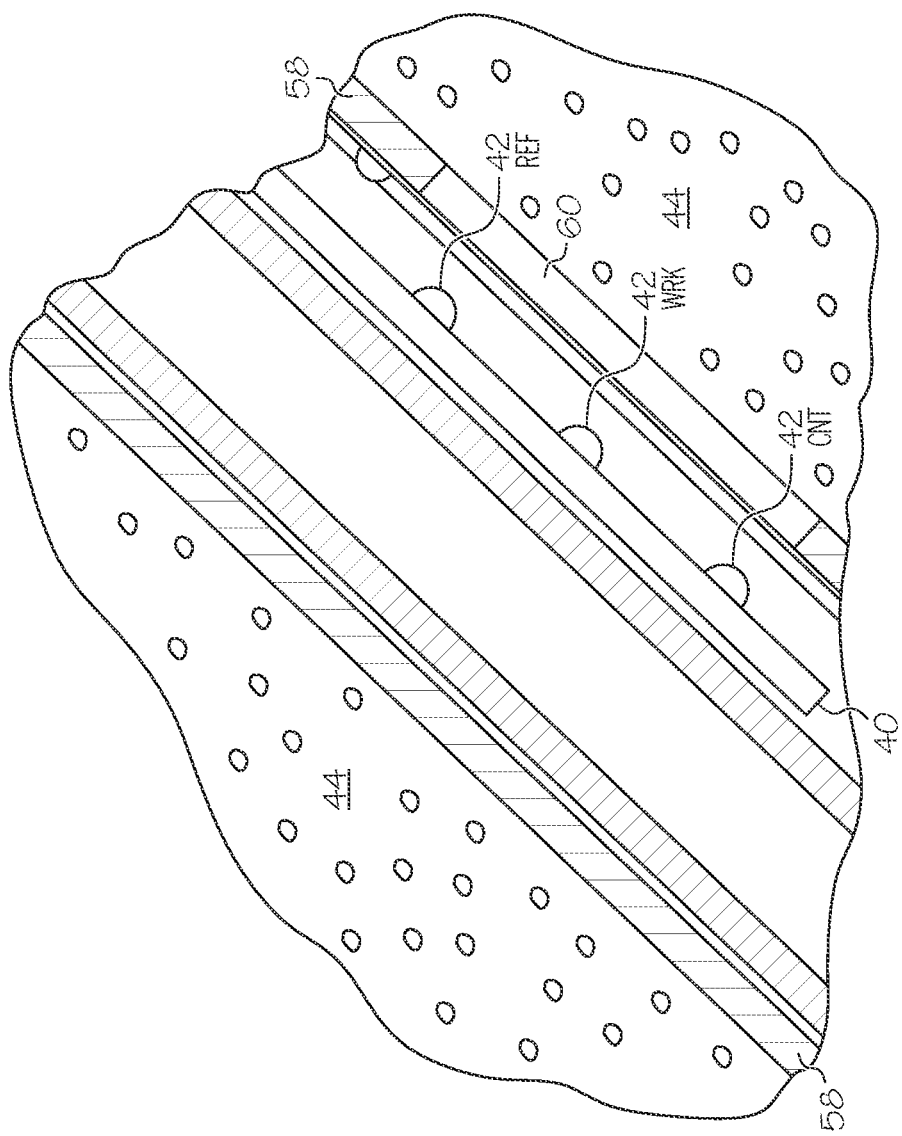
FIG. 4 is a cross sectional view of a sensing end of a sensor set of FIG. 3D for an embodiment.
Figure 5:
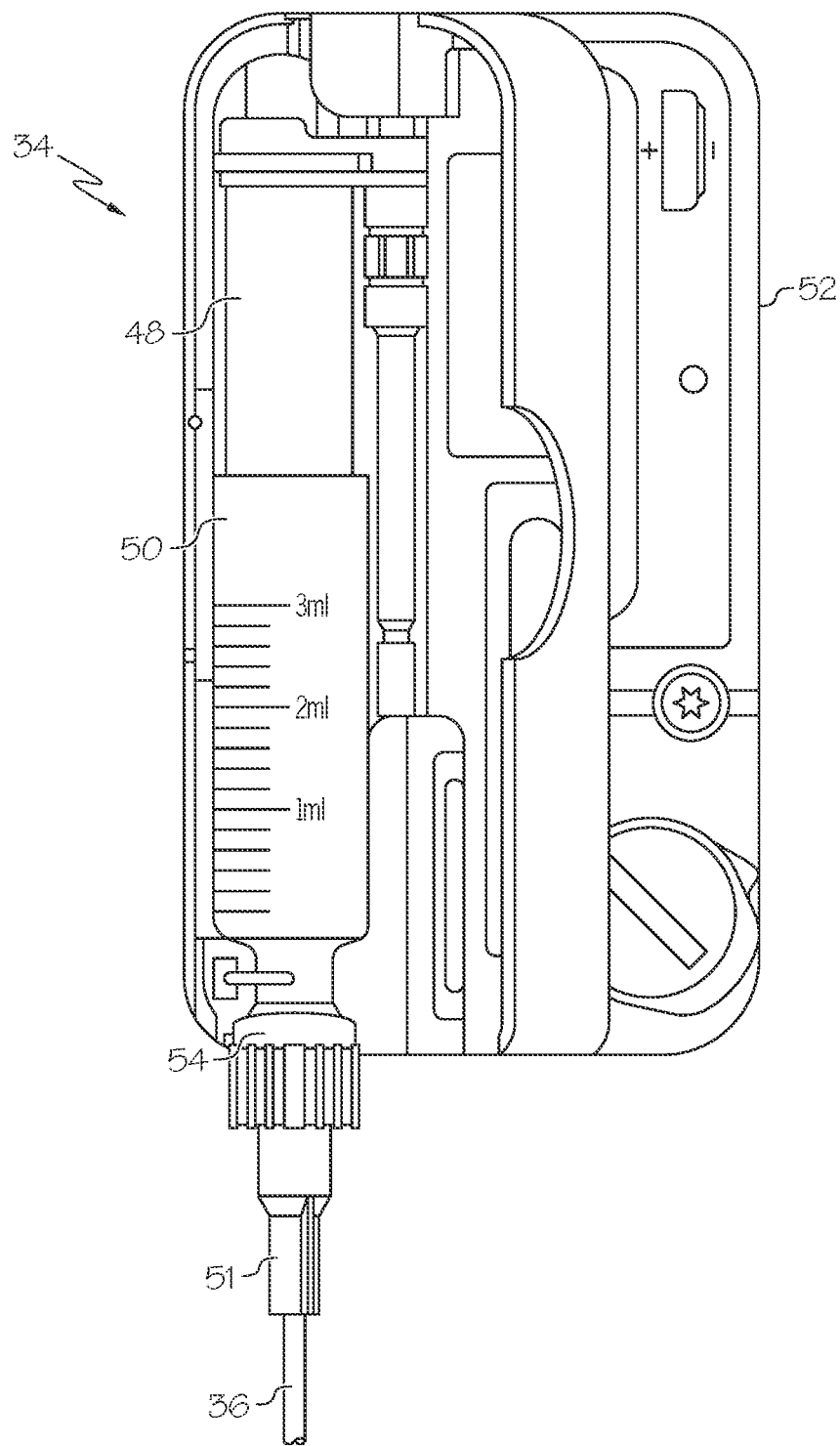
FIG. 5 is a top view of an infusion device with a reservoir door in an open position, for use according to an embodiment.
Figure 6:
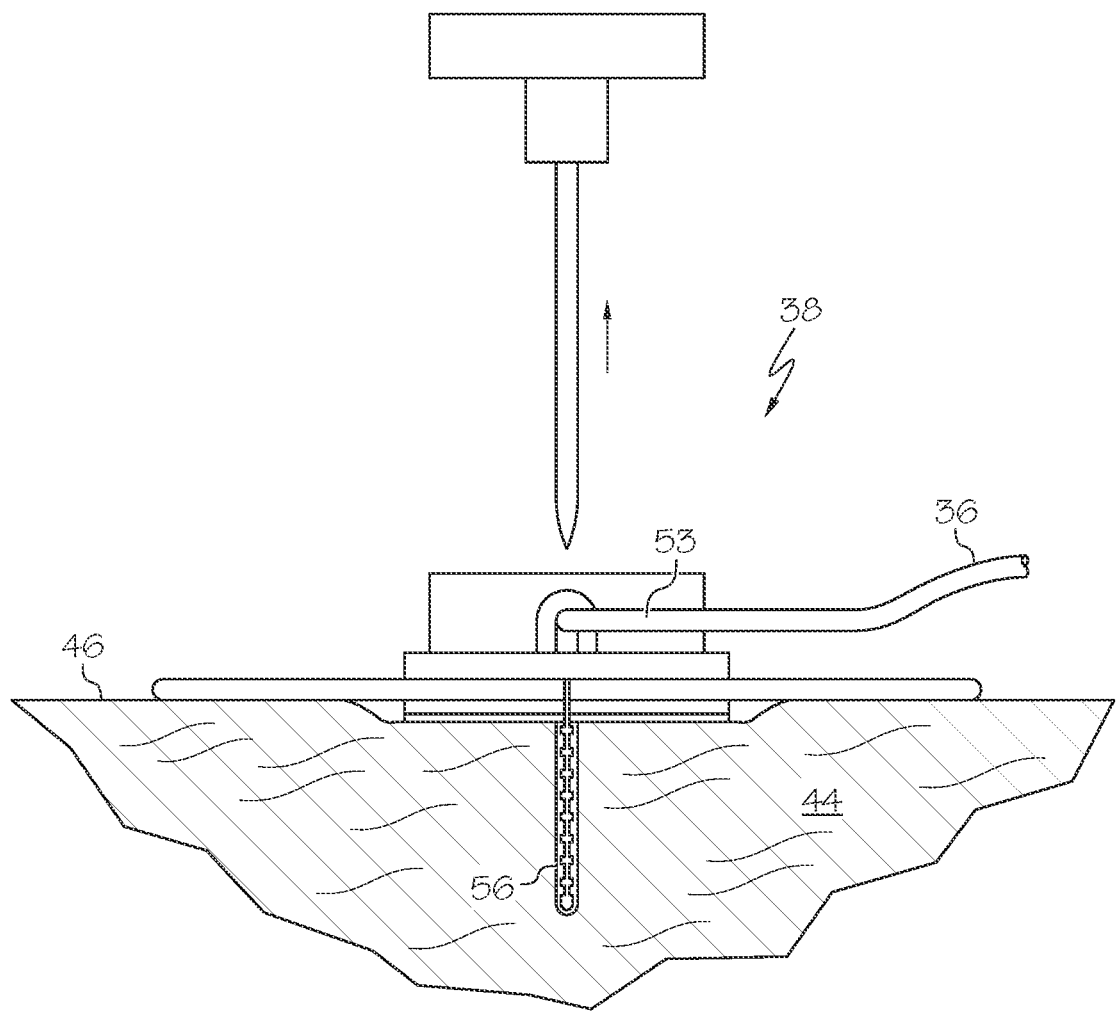
FIG. 6 is a side view of an infusion set with an insertion needle pulled out, for use according to an embodiment.

FIGS. 2-6 illustrate glucose control systems in accordance with certain embodiments. Such glucose control systems may be used, for example, in controlling a patient's glucose level about a target range as discussed above. It should be understood, however, that these are merely examples of particular systems that may be used for controlling a patient's glucose level about a target range and that claimed subject matter is not limited in this respect. FIG. 2 is a front view of closed loop hardware located on a body in accordance with certain embodiments. FIGS. 3A-3D and 4 show different views and portions of an exemplary glucose sensor system for use in accordance with certain embodiments. FIG. 5 is a top view of an infusion device with a reservoir door in an open position in accordance with certain embodiments. FIG. 6 is a side view of an infusion set with an insertion needle pulled out in accordance with certain embodiments.

Particular embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3A and 3B, telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3D and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3C and 3D. Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 1, 2, and 5, a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucagon may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 20 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 20.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Pat. No. 7,833,157; entitled "MULTILUMEN CATHETER", may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Certain examples of system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that may contribute to a sensor measurement lagging behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches by application of a predicted duration of a blood glucose level being outside of a target range to better address a patient's glycemic health.

Figure 7:
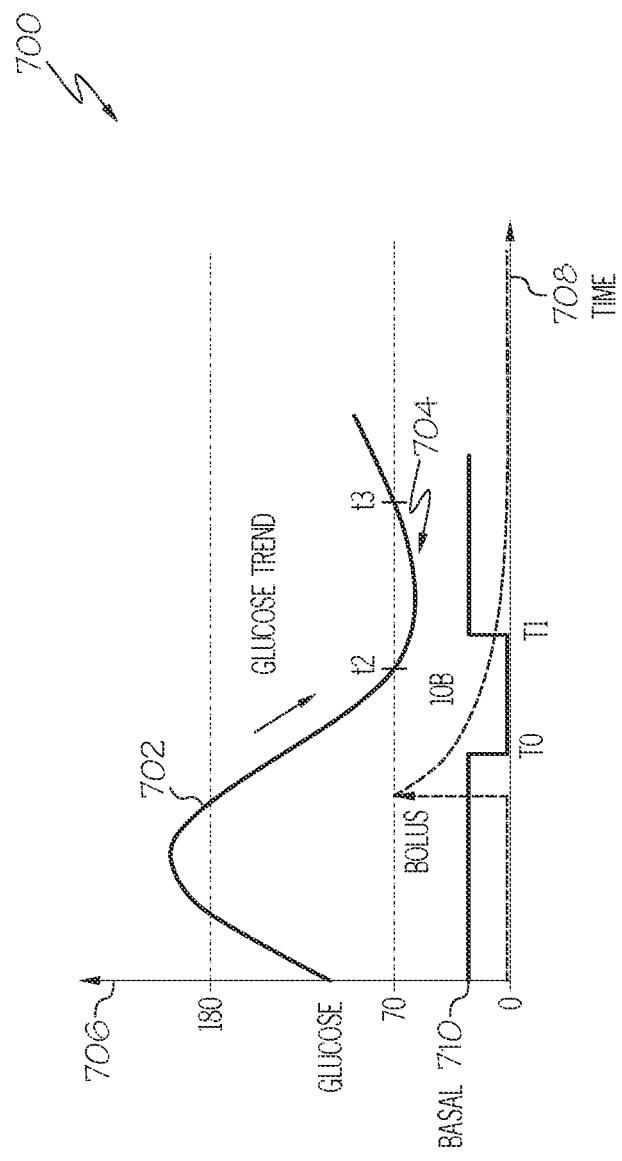
FIG. 7 is a plot of a trajectory of a blood glucose trend including a period of hypoglycemia that is not rectified by suspension of a continuous basal insulin delivery.

FIG. 7 is a plot 700 of a trajectory of a blood glucose trend 702 including a period of hypoglycemia 704 that is not rectified by suspension of a continuous basal insulin delivery. The plot 700 shows the glucose trend 702 as a plurality of blood glucose levels 706, for a particular user, over time 708. The blood glucose levels 706 associated with the glucose trend 702 are obtained by blood glucose sensors of an insulin delivery pump. As shown, the glucose trend 702 increases from the origin to a glucose level 706 above 180 milligrams per deciliter (mg/dL), and then decreases to a glucose level 706 below 70 mg/dL. The glucose levels 706 below 70 mg/dL indicate low blood glucose for a duration of time between time $t_3$ and time $t_4$ (e.g., the period of hypoglycemia 704).

The plot 700 also illustrates a continuous basal insulin delivery 710 that is suspended (i.e., the basal insulin delivery 710 stops) at time $t_0$, and remains suspended until time $t_1$. Here, the basal insulin plot is superimposed for consistency with the time scale, but is not measured according to the vertical scale. The basal insulin is plotted using Units per hour (Unit/h). The bolus insulin and insulin on board (IOB) are also plotted using Unit as the vertical scale.

The purpose of the suspension is to address the decreasing blood glucose levels 706 that are shown by the glucose trend 702. However, in this example, the glucose trend 702 continues to decrease and remains in a hypoglycemic state for a duration of time 708 (e.g., the period of hypoglycemia 704), and the suspension of the basal insulin delivery 710 at time $t_0$ did not stop the occurrence of the period of hypoglycemia 704. In this situation, the glucose trend 702 shows blood glucose levels 706 below 70 mg/dL until time $t_3$, at which point the glucose trend 702 is increasing and passes through the 70 mg/dL threshold, at which point (e.g., time point $t_3$) the period of hypoglycemia 704 has ended.

The plot 700 depicts one particular instance where suspension of the continuous basal insulin delivery 710 by itself is not enough to stop a period of hypoglycemia 704 from occurring. When this scenario occurs, additional actions may be required to prevent a period of hypoglycemia, or to rectify a current period of hypoglycemia. An insulin delivery pump may take other actions to rectify the anticipated period of hypoglycemia, in combination with the suspension of the basal insulin delivery 710. For example, the insulin delivery pump may provide a glucagon injection, or other type of blood glucose medication, or generate an alert so that a user can take additional actions (e.g., the user may choose to ingest fruit juice or blood glucose medication, in response to the alert).

Figure 8:
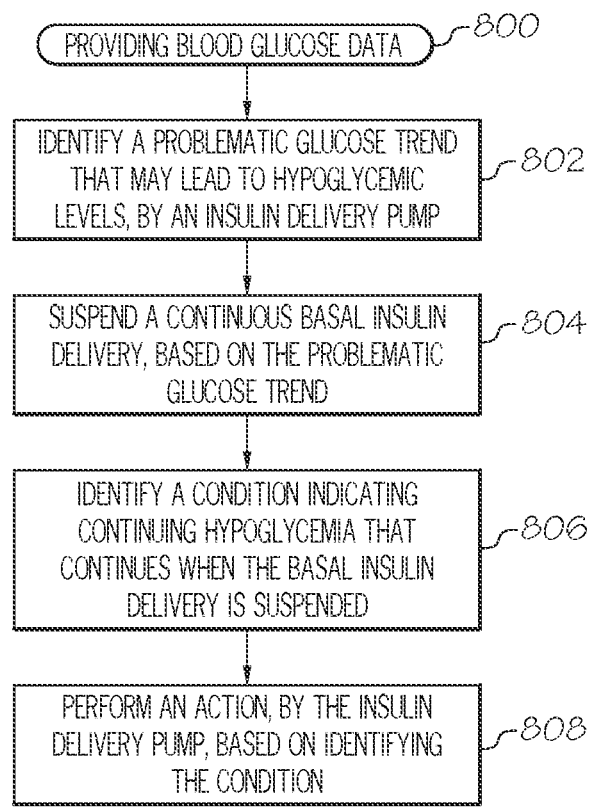
FIG. 8 is a flow chart that illustrates an exemplary embodiment of a process for providing blood glucose data.

FIG. 8 is a flow chart that illustrates an exemplary embodiment of a process 800 for providing blood glucose data. The various tasks performed in connection with process 800 may be performed by software, hardware, firmware, or any combination thereof. For illustrative purposes, the following description of process 800 may refer to elements mentioned above in connection with FIGS. 1-7. In practice, portions of process 800 may be performed by different elements of the described system. It should be appreciated that process 800 may include any number of additional or alternative tasks, the tasks shown in FIG. 8 need not be performed in the illustrated order, and process 800 may be incorporated into a more comprehensive procedure or process having additional functionality not described in detail herein. Moreover, one or more of the tasks shown in FIG. 8 could be omitted from an embodiment of the process 800 as long as the intended overall functionality remains intact.

First, the process 800 identifies a problematic glucose trend that may lead to hypoglycemic levels, by an insulin delivery pump (step 802). The insulin delivery pump is communicatively coupled to a subcutaneous sensor, and is continuously monitoring blood glucose levels of the user of the insulin delivery pump via the subcutaneous sensor (as described previously, with regard to FIGS. 1-6). In certain embodiments, the insulin delivery pump is configured to obtain blood glucose levels for the user, via the subcutaneous sensors, at timed intervals. In some embodiments, however, the insulin delivery pump may be activated to obtain blood glucose levels in response to an input user request. As the blood glucose levels are obtained, the process 800 continuously calculates a rate of change for the blood glucose levels. The rate of change for the blood glucose levels may be referred to as the glucose trend. A problematic glucose trend is a glucose trend which is decreasing at a rapid rate. In exemplary embodiments of the present disclosure, a glucose trend that is decreasing at a rapid rate may be defined as a sensor rate of change below −1 milligrams per deciliter (mg/dL), per minute.

Next, the process 800 suspends a continuous basal insulin delivery, based on the problematic glucose trend (step 804). The insulin delivery pump is configured to automatically suspend basal insulin delivery when sensor glucose levels are predicted to approach a low limit, and to resume basal insulin delivery once sensor glucose levels recover. Thus, the insulin delivery pump functions to reduce hypoglycemic events and to reduce time spent in the hypoglycemic range. Here, the process 800 predicts that sensor glucose levels will approach a low limit, based on the identified problematic glucose trend (step 802), and, in response, suspends basal insulin delivery.

The process 800 then identifies a condition indicating a continuing hypoglycemia that continues when the basal insulin delivery is suspended (step 806). One suitable methodology for identifying the condition is described below with reference to FIG. 9. A second suitable methodology for identifying the condition is described below with reference to FIG. 10. Here, the insulin delivery pump is aware of a predicted, upcoming hypoglycemic event, and the process 800 determines that the hypoglycemic event will continue after the insulin delivery pump reacts to the upcoming hypoglycemic event by suspending basal insulin delivery. In other words, the suspension of the basal insulin delivery is insufficient to prevent the period of hypoglycemia, and additional treatment is required to address the hypoglycemic event.

After identifying the condition (step 806), the process 800 performs an action, by the insulin delivery pump, based on identifying the condition (step 808). The action may include presenting an alert, by the insulin delivery pump. The alert may include an audio alert, a visual alert, or any combination thereof. Exemplary embodiments may include a "pop-up" message presented on a display of the insulin delivery pump, a voice communication informing the user of the condition, and/or an alarm that sounds when the condition is detected.

Figure 9:
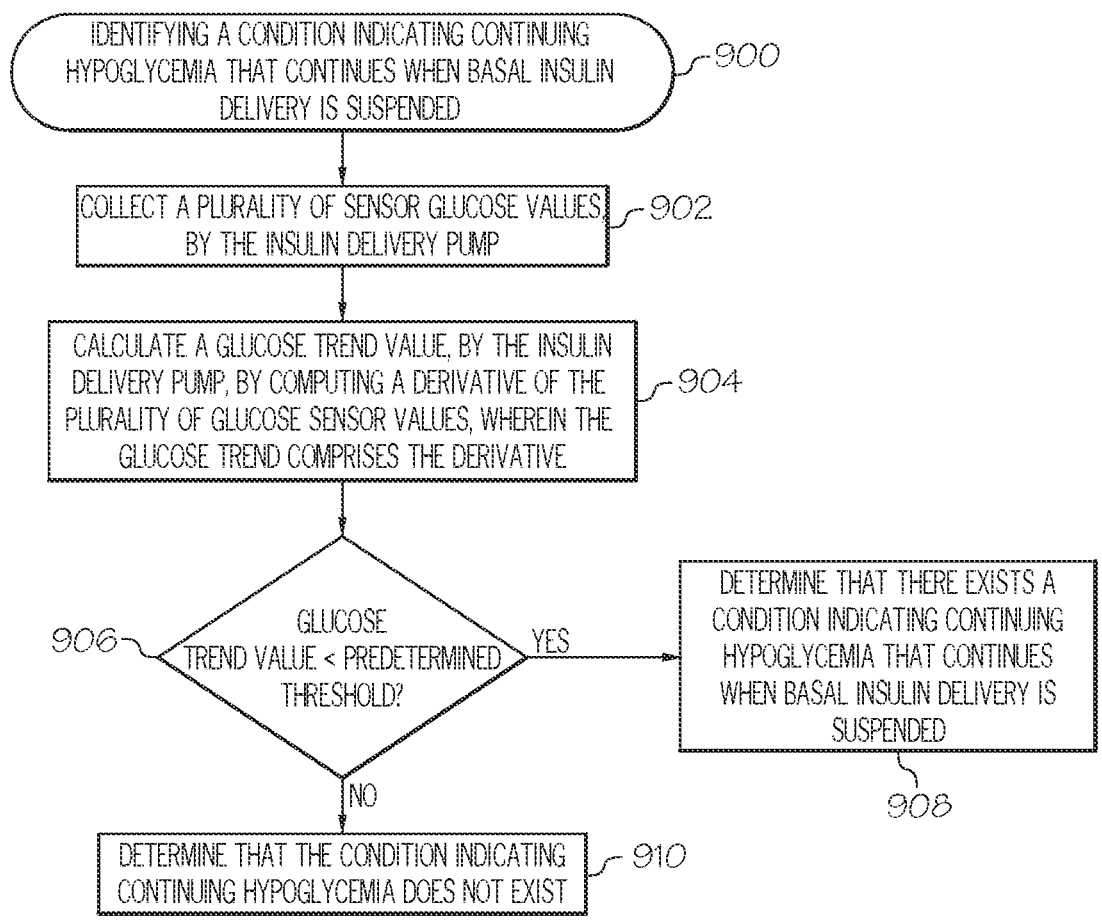
FIG. 9 is a flow chart that illustrates an exemplary embodiment of a process for identifying a condition indicating continuing hypoglycemia that continues when basal insulin delivery is suspended.

FIG. 9 is a flow chart that illustrates an exemplary embodiment of a process 900 for identifying a condition indicating continuing hypoglycemia that continues when basal insulin delivery is suspended. It should be appreciated that the process 900 described in FIG. 9 represents one embodiment of step 806 described above in the discussion of FIG. 8, including additional detail. First, the process 900 collects a plurality of sensor glucose values, by the insulin delivery pump (step 902), for purposes of determining a glucose trend which is used to detect missed hypoglycemic events. The glucose trend is one of the dominant factors of severity of impending hypoglycemia, and thus may be used to detect a hypoglycemic event during which suspension of basal insulin delivery is insufficient to prevent or rectify the hypoglycemic event. The glucose trend may also be referred to as a glucose rate of change and/or a glucose derivative.

Next, the process 900 calculates a glucose trend value by computing a derivative of the plurality of glucose sensor values, wherein the glucose trend comprises the derivative (step 904). The calculation of the derivative of the plurality of glucose sensor values is a commonly used glucose trend calculation technique that is well-known in the industry. Generally, the insulin delivery pump performs these calculations using an internally integrated controller or processor (see FIG. 1), and presents the results of the calculations via a display device communicatively coupled to the controller. In certain embodiments, the insulin delivery pump presents, via the display device, glucose trend information as one or more graphical elements (e.g., arrows). For example, one arrow pointing up indicates that the glucose trend (i.e., glucose rate of change) is greater than 1 mg/dL per minute, and one arrow pointing down indicates that the glucose trend is less than −1 mg/dL per minute. Thus, the glucose trend is generally readily available information that is provided by an insulin delivery pump.

The process 900 then determines whether the glucose trend value is less than a predetermined threshold (decision 906). The predetermined threshold is obtained by analyzing actual insulin delivery pump data, and identifying a threshold that indicates hypoglycemia, based on the analysis.

When the glucose trend value is not less than the predetermined threshold (the "No" branch of 906), the process 900 determines that the condition indicating continuing hypoglycemia does not exist (step 910). However, when the glucose trend value is less than the predetermined threshold (the "Yes" branch of 906), the process 900 determines that there exists a condition indicating continuing hypoglycemia that continues when basal insulin delivery is suspended (step 908). Here, the process 900 determines that blood glucose levels decrease to a point below a "suspension threshold" (i.e., a threshold point at which the insulin delivery pump suspends basal insulin delivery). Due to a rapid decrease in the glucose trend detected by the process 900, the process 900 predicts the existence of a condition in which blood glucose levels will continue to decrease, thereby inducing hypoglycemia.

Figure 10:
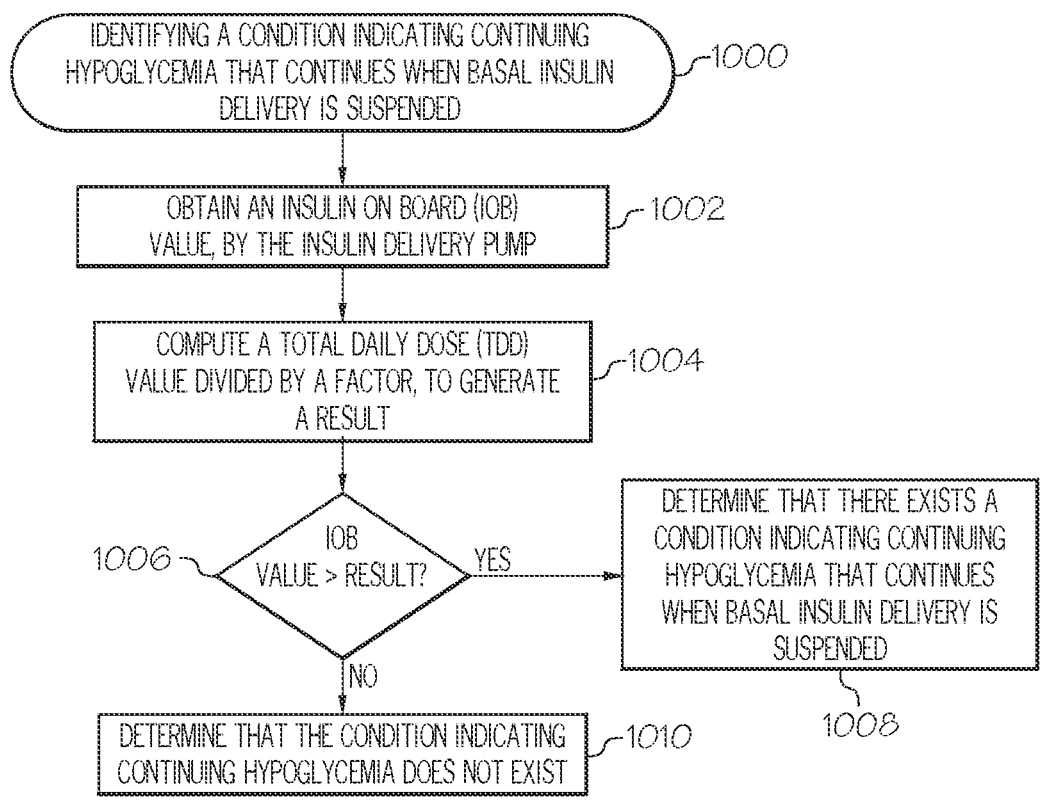
FIG. 10 is a flow chart that illustrates another exemplary embodiment of a process for identifying a condition indicating continuing hypoglycemia that continues when basal insulin delivery is suspended.

FIG. 10 is a flow chart that illustrates another exemplary embodiment of a process 1000 for identifying a condition indicating continuing hypoglycemia that continues when basal insulin delivery is suspended. It should be appreciated that the process 1000 described in FIG. 10 represents one embodiment of step 806 described above in the discussion of FIG. 8, including additional detail. The process 1000 uses glucose trend values and insulin on board (IOB) values to identify the condition indicating continuing hypoglycemia that continues when basal insulin delivery is suspended. This is because the blood glucose trend and the IOB value are two fundamental conditions that can cause a hypoglycemic event. In other embodiments, there could be other states associated with a hypoglycemic event, such as a predicted glucose value or a plasma insulin value. However, the predicted glucose value and the plasma insulin value provide the same information for analysis. Blood glucose trend values and IOB values are used because the information is readily available from a standard insulin delivery pump and require no additional calculations.

First, the process 1000 obtains an insulin on board (IOB) value, by the insulin delivery pump (step 1002), which is used to detect missed hypoglycemic events. An insulin on board (IOB) value is a quantity of insulin remaining in the body of the user following a bolus of insulin provided by the insulin delivery pump. The IOB value is one of the dominant factors of severity of impending hypoglycemia, and thus may be used to detect a hypoglycemic event during which suspension of basal insulin delivery is insufficient to prevent or rectify the hypoglycemic event. The insulin on board (IOB) value reflects the current effective insulin existing inside the body which will keep lowering blood glucose values. The higher the IOB value is, the faster blood glucose levels will drop.

Next, the process 1000 computes a total daily dose (TDD) value divided by a factor, to generate a result (step 1004). A total daily dose (TDD) value is a quantity of insulin required by the user in a twenty-four (24) hour period. TDD is a factor that reflects how sensitive the patient is to insulin. The higher the TDD value is, the more insulin the patient requires to compensate for blood glucose in the body of the patient.

The process 1000 then determines whether the IOB value is greater than the result (decision 1006). Here, the process 1000 is comparing the quantity of insulin remaining in the body (i.e., IOB) to the quantity of insulin required by the user in a 24-hour period (i.e., TDD), to predict a potential insufficient response to a hypoglycemic event. The TDD value reflects insulin sensitivity of the patient. Thus, the IOB value needs to be above the patient dependent factor to have a significant effect on compensating same amount of glucose. For example, an IOB value of 5 units is enough to drop the blood glucose levels very quickly for a patient with 20 units TDD, but will not have the same effect (e.g., will not drop blood glucose levels very quickly) for a patient with 60 units TDD.

When the IOB value is not greater than the result (the "No" branch of 1006), the process 1000 determines that the condition indicating continuing hypoglycemia does not exist (step 1010). However, when the IOB value is greater than the result (the "Yes" branch of 1006), the process 1000 determines that there exists a condition indicating continuing hypoglycemia that continues when basal insulin delivery is suspended (step 1008). Here, the process 1000 determines that blood glucose levels decrease to a point below a "suspension threshold" (i.e., a threshold point at which the insulin delivery pump suspends basal insulin delivery). Due to a large IOB value detected by the process 1000, the process 1000 predicts the existence of a condition in which blood glucose levels will continue to decrease, thereby inducing hypoglycemia.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium", "processor-readable medium", or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

The following description refers to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. Likewise, unless expressly stated otherwise, "connected" means that one element/node/feature is directly joined to (or directly communicates with) another element/node/feature, and not necessarily mechanically. Thus, although each of the schematics shown in FIGS. 1-6 depict one exemplary arrangement of elements, additional intervening elements, devices, features, or components may be present in an embodiment of the depicted subject matter.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A system comprising:
one or more processors; and
one or more processor-readable storage media storing instructions which, when executed by the one or more processors, cause performance of:
obtaining, by a controller associated with an insulin delivery pump, an amount of insulin remaining in a body of a patient;
obtaining, by the controller, a quantity of insulin needed by the patient within a future time period;
based on determining that the amount of insulin remaining in the body is greater than the quantity of insulin needed by the patient within the future time period, identifying, by the controller, a condition in which the patient's glucose level will continue to decrease during the future time period despite suspension of basal insulin dosage delivery; and
responsive to identifying the condition, causing, by the controller, performance of an action for preventing the patient's glucose level from falling into a hypoglycemic range in combination with the suspension of basal insulin dosage delivery.

2. The system of claim 1, wherein the one or more processor-readable storage media further store instructions which, when executed by the one or more processors, cause performance, by the controller, of:
prior to identifying the condition, causing to suspend the basal insulin dosage delivery based on identifying a glucose trend in the patient toward the hypoglycemic range.

3. The system of claim 2, wherein identifying the glucose trend in the patient comprises:
obtaining, by the controller, a plurality of glucose values;
calculating, by the controller, a glucose trend value based on computing a derivative of the plurality of glucose values; and
comparing, by the controller, the glucose trend value to a hypoglycemia threshold.

4. The system of claim 1, wherein causing the performance of the action comprises communicating, by the controller, a command to a medication delivery device.

5. The system of claim 1, wherein the action comprises delivering glucagon to the patient by a glucagon delivery system.

6. The system of claim 1, wherein the action comprises presenting, via the insulin delivery pump, a recommendation to ingest a substance for increasing the patient's glucose level.

7. The system of claim 1, wherein the amount of insulin remaining in the body is represented as an insulin-on-board (IOB) value corresponding to a quantity of insulin remaining in the patient following delivery of a bolus of insulin.

8. The system of claim 1, wherein the quantity of insulin needed by the patient is calculated, by the controller, based on a total daily dose (TDD) value that is scaled by a factor to result in a value that is less than the TDD value, wherein the TDD value is a quantity of insulin to be delivered to the patient by the insulin delivery pump in a twenty-four hour period.

9. One or more processor-readable storage media storing instructions which, when executed by one or more processors, cause performance of:
obtaining, by a controller associated with an insulin delivery pump, an amount of insulin remaining in a body of a patient;
obtaining, by the controller, a quantity of insulin needed by the patient within a future time period;
based on determining that the amount of insulin remaining in the body is greater than the quantity of insulin needed by the patient within the future time period, identifying, by the controller, a condition in which the patient's glucose level will continue to decrease during the future time period despite suspension of basal insulin dosage delivery; and
responsive to identifying the condition, causing, by the controller, performance of an action for preventing the patient's glucose level from falling into a hypoglycemic range in combination with the suspension of basal insulin dosage delivery.

10. The one or more processor-readable storage media of claim 9, further storing instructions which, when executed by the one or more processors, cause performance of:
prior to identifying the condition, causing, by the controller, the insulin delivery pump to suspend the basal insulin dosage delivery based on identifying a glucose trend in the patient toward the hypoglycemic range.

11. The one or more processor-readable storage media of claim 9, wherein the amount of insulin remaining in the body is represented as an insulin-on-board (IOB) value corresponding to a quantity of insulin remaining in the patient following delivery of a bolus of insulin.

12. The one or more processor-readable storage media of claim 9, wherein the quantity of insulin needed by the patient is calculated, by the controller, based on a total daily dose (TDD) value that is scaled by a factor to result in a value that is less than the TDD value, wherein the TDD value is a quantity of insulin to be delivered to the patient by the insulin delivery pump in a twenty-four hour period.

* * * * *